United States Patent [19]
Stack et al.

[11] Patent Number: 4,797,488
[45] Date of Patent: Jan. 10, 1989

[54] PSYCHOTROPIC POLYCYCLIC IMIDES

[75] Inventors: Gary P. Stack, Merion; Thomas D. Golobish, Devon, both of Pa.; Magid A. Abou-Gharbia, Wilmington, Del.

[73] Assignee: American Home Products Corporation, New York, N.Y.

[21] Appl. No.: 34,820

[22] Filed: Apr. 3, 1987

[51] Int. Cl.$^4$ .................. C07D 401/14; C07D 403/14; C07D 413/14; C07D 417/14

[52] U.S. Cl. ...................................... 544/295; 544/14; 544/32; 544/99; 544/101; 544/230; 544/257; 544/361; 544/363; 549/240; 562/498

[58] Field of Search ..................... 544/295, 14, 32, 99, 544/101, 230, 357, 361, 363

[56] References Cited

U.S. PATENT DOCUMENTS

| | | | |
|---|---|---|---|
| 4,507,303 | 3/1985 | Ishizumi et al. | 544/230 |
| 4,562,255 | 12/1985 | Freed et al. | 544/357 |
| 4,675,403 | 6/1987 | Abou-Gharbia et al. | 544/230 |
| 4,732,983 | 3/1988 | Stack et al. | 544/295 |
| 4,732,984 | 3/1988 | Abou-Gharbia et al. | 544/364 |
| 4,748,240 | 5/1988 | Stack et al. | 544/295 |

FOREIGN PATENT DOCUMENTS

| | | |
|---|---|---|
| 2057845 | 6/1971 | Fed. Rep. of Germany . |
| 60-87262 | 5/1985 | Japan . |
| 7017031 | 11/1969 | Netherlands . |

OTHER PUBLICATIONS

Korgaonkar et al., "Chemical Abstracts", vol. 101, 1984, col. 101:23432k.

Primary Examiner—Richard L. Raymond
Assistant Examiner—James H. Turnipseed
Attorney, Agent, or Firm—Richard K. Jackson

[57] ABSTRACT

Substituted imides of the following formula are antipsychotic, anxiolytic agents with very little extrapyramidal side effects:

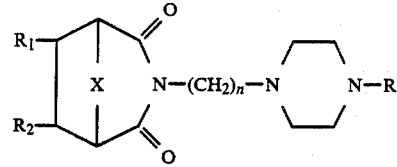

in which X is —O—, —S—, —SO—, —SO$_2$—, —CR$_3$R$_4$— where R$_3$ and R$_4$, independently, are hydrogen, alkyl of 1 to 4 carbon atoms or, taken together with the carbon atom to which they are attached, R$_3$ and R$_4$ form a cycloalkyl group of of 3 to 5 carbon atoms; n is one of the integers 2, 3, 4 or 5; R is phenyl, halophenyl, trifluoromethylphenyl, alkoxyphenyl in which the alkoxy substituent contins 1 to 3 carbon atoms, 2-pyrimidinyl, halopyrimidin-2-yl, 2-pyrazinyl, halopyrazin-2-yl, 2-pyridinyl, cyanopyridin-2-yl, halopyridin-2-yl, quinolyl, or haloquinolyl; R$_1$ and R$_2$, taken together, are alkylene of 3 to 5 carbon atoms or alkenylene of 3 to 5 carbon atoms, or taken with the carbon atoms to which they are attached, R$_1$ and R$_2$ complete a benzene ring, or a group of the formula:

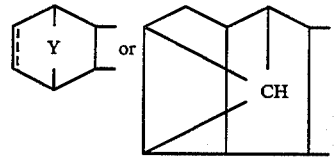

where Y is —CH$_2$—, —CH$_2$—CH$_2$—, —O— or —S— and the dotted line represents optional unsaturation; or a pharmaceutically acceptable salt thereof. In addition, the intermediate b3-dicarboxylic and the corresponding anhydrides - 2,3,3a,3b,4,5,6,6a,7,7a-decahydro-4,6,7-metheno-1H-cyclopenta[a]pentalene-1,3-dicarboxylic acid and octahydro-1,5-methano-6,8,9-metheneopentaleno[1,2-d]oxepin-2,4(1H,5H)-dione represent especially significant aspects of the invention.

17 Claims, No Drawings

PSYCHOTROPIC POLYCYCLIC IMIDES

BACKGROUND OF THE INVENTION

Netherlands Pat. No. 7,017,031 discloses 8-(heteroarylpiperazinylalkyl)-8-azaspiro[4,5]decane-7,9-diones as tranquilizers and anti-emetics.

Japanese Pat. No. 60/87262 (C.A. 103: 215155K) discloses N-(heteroarylpiperazinylalkyl)cycloalkanosuccinimide derivatives as having anti-conflict activity.

DESCRIPTION OF THE INVENTION

In accordance with this invention there is provided a group of antipsychotic, anxiolytic N-(aryl and heteroarylpiperazinylalkyl)polycyclic-1,3-dicarboxylic acid imides of the formula:

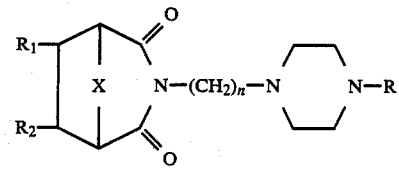

in which
X is —O—, —S—, —SO—, —SO$_2$—, —CR$_3$R$_4$— where R$_3$ and R$_4$, independently, are hydrogen, alkyl of 1 to 4 carbon atoms or, taken together with the carbon atom to which they are attached, R$_3$ and R$_4$ form a cycloalkyl group of 3 to 5 carbon atoms;
n is one of the integers 2, 3, 4 or 5;
R is phenyl, halophenyl, trifluoromethylphenyl, alkoxyphenyl in which the alkoxy substituent contains 1 to 3 carbon atoms, 2-pyrimidinyl, halopyrimidin-2-yl, 2-pyrazinyl, halopyrazin-2-yl, 2-pyridinyl, cyanopyridin-2-yl, halopyridin-2-yl, quinolyl, or haloquinolyl;
R$_1$ and R$_2$, taken together, are alkylene of 3 to 5 carbon atoms or alkenylene of 3 to 5 carbon atoms, or taken with the carbon atoms to which they are attached, R$_1$ and R$_2$ complete a benzene ring, or a group of the formula

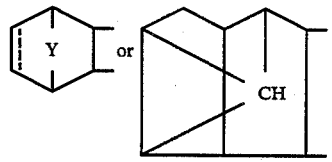

where Y is —CH$_2$—, —CH$_2$—CH$_2$—, —O— or —S— and the dotted line represents optional unsaturation; or a pharmaceutically acceptable salt thereof. In these compounds, the R$_1$-R$_2$ ring juncture is either endo or exo with respect to either of the bicyclic rings.

The preferred compounds of the genus of this invention are those which X is —CH$_2$; n is 3, 4 or 5 and most preferrably 4; and R$_1$ and R$_2$, taken with the carbon atoms to which they are attached, complete a cyclic alkane, alkene or aromatic hydrocarbon ring containing 5 to 10 carbon atoms, such as cyclopentane, cyclopentene, norbornane, norbornene, perhydrometheno-pentalene, benzene, and the like. Of the halogen substituents fluoro, chloro and bromo, chloro is preferred. The pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

Among the several intermediate 1,3-dicarboxylic acids prepared pursuant to obtaining the end products of this invention, of special interest is the compound 2,3,3a, 3b, 4,5,6,6a,7,7a-decahydro-4,6,7-metheno-1H-cyclopenta[a]pentalene-1,3-dicarboxylic acid—

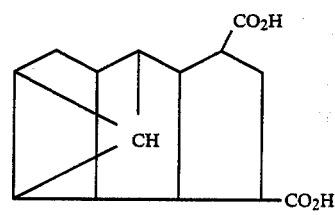

—and its corresponding anhydride, which are useful in preparation of several of the herein disclosed compounds as well as the most preferred, single embodiment of this invention disclosed in Example 6, infra.

The compounds of the invention are prepared by conventional methods. For example, a suitable polycyclic 1,3-dicarboxylic acid, or the anhydride derived from it, is combined with the desired piperazinyl alkyl amine in a high boiling solvent such as toluene or xylene and refluxed for an extended period with either chemical (e.g. ethoxyacetylene) or mechanical (e.g. Dean-Stark trap) water removal, thusly:

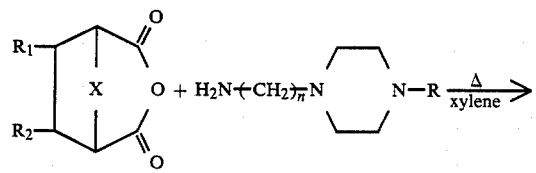

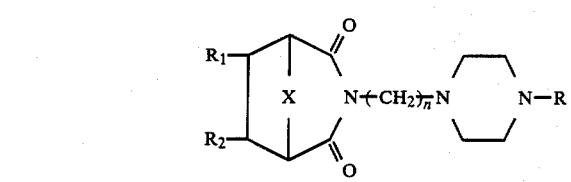

Alternatively, the compounds of this invention are readily prepared from the appropriate polycyclic imide via alkylation with a suitable dihalo lower alkane in the presence of a strong base such as sodium hydride, followed by reaction of the intermediate product with the desired aryl- or heteroaryl substituted piperazine, thusly:

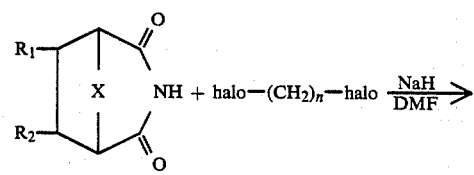

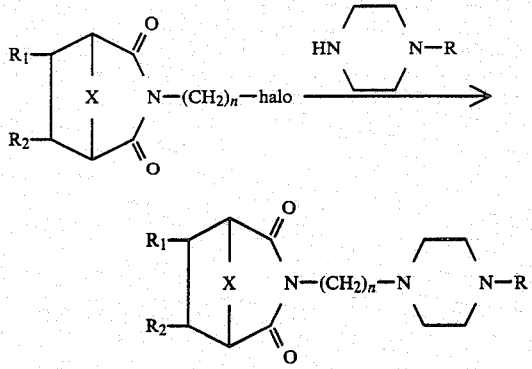

The polycyclic 1,3-dicarboxylic acids themselves are known compounds or they can be prepared from the appropriate polycyclic olefin by treatment with a suitable oxidizing agent such as potassium permanganate or ruthenium tetroxide (or from the appropriate polycyclic ketone by treatment with potassium permanganate or from the appropriate diketone via treatment with periodic acid).

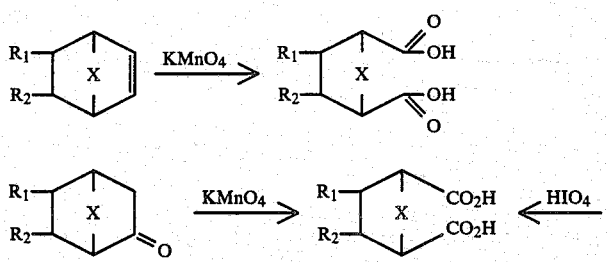

The antipsychotic properties of the compounds of this invention were established by standard pharmacologically accepted procedures involving conditioned avoidance studies in which trained male CD rats (Charles River), 400–450 g. body weight are exposed to a fifteen second warning tone (conditioned stimulus) continued for an additional fifteen seconds accompanied by electric shock. The rat can avoid the electric shock by jumping to an exposed shelf (shelf-jump response). A response during the initial warning tone is considered an avoidance response, while a response during shock delivery is considered as escape response. The shelf-jump response test procedure follows that of Herman et al., Comm. in Psychopharm., 3, pp. 165–171 (1979). The compounds of this invention were tested at a single dose (40 mg./kg. i.p.) in this procedure and were rated relative to their inhibition of conditioned avoidance responding. A similar test procedure in which a lever press was substituted for a shelf-jump was used to establish the oral (p.o) activity of the test compounds. Orally active compounds were tested over a full dose range and the Avoidance Block activities reported as "$AB_{50}$'s" (mg./kg.).

As a further measure of antipsychotic activity, the compounds of this invention were also studied as antagonists of apomorphine-induced stereotyped behavior and climing wherein CF-1 mice (Charles River) receive the test compound i.p. at several dose levels (1, 10, 30 and 60 mg./kg.) (six mice per dose level) and thirty minutes later receive 1 mg./kg. apomorphine s.c. Five minutes after injection, the sniffing-licking-gnawing syndrome and climbing behavior induced by apomorphine are scored for each animal. Readings are repeated every five minutes during a thirty minute test session. An $ED_{50}$ value (with 95% confidence intervals) is calculated for inhibition of apomorphine-induced stereotyped behavior and climbing using a non-linear least squares calculation with inverse prediction. The ratio of the $ED_{50}$ for stereotyped behavior to the $ED_{50}$ for climbing is calculated. High ratios indicate antipsychotic activity with low liability for the extrapyramidal side effects which attend long term treatment with such standard antipsychotic drugs as haloperidol (ratio=1.00), chlorpromazine (ratio=1.51) and thioridazine (ratio=1.83).

In further support of the low potential for side-effects exhibited by the compounds of this invention, representative compounds were established to exhibit only weak binding to the D-2 dopamine receptor when tested in accordance with a modification of the procedure of Fields et al., Brain Res., 136, pp. 578–584 (1977) and Yamamura et al., eds., Neurotransmitter Receptor Binding, Raven Press, N.Y. (1978), wherein homogenized limbic brain tissue is incubated with $^3$H-spiroperidol and various concentrations of test compound, filtered and washed and shaken with Hydrofluor scintillation cocktail (National Diagnostics) and counted in a Packard 460CD scintillation counter. The results of this testing with compounds representative of the invention whose production is exemplified, infra, are as follows:

| | Conditioned Avoidance | | Apomorphine Antagonism | | [$^3$H] Spiroperidol Binding Inhibition |
|---|---|---|---|---|---|
| | Shelf-Jump 40 mg/kg, | Discrete Trial $AB_{50}$ | $ED_{50}$, mg/kg, p.o. | | $K_i$, nM or |
| Ex. | i.p. | p.o. | Stereotypy | Climbing | % at 1 μM |
| 1 | >20% | 40.06 | inactive | 4.08 | 54% |
| 2 | >20% | inactive | inactive | 24.21 | 20% |
| 3 | ~80% | inactive | 30.87 | 4.91 | 23% |
| 4 | ~80% | weak | inactive | 5.50 | 59% |
| 5 | >20% | active | inactive | 47.17 | 25% |
| 6 | ~80% | 33.76 | inactive | 0.40 | 56 nM |
| 7 | >20% | inactive | inactive | inactive | 54% |
| 8 | >20% | inactive | inactive | inactive | 23% |
| 9 | >20% | | inactive | >50 | 0% |
| 10 | >20% | inactive | 10.00 | 4.71 | 18 nM |
| 11 | >20% | 46.17 | 42.37 | 18.89 | 100% |
| 12 | <20% | | inactive | inactive | 30 nM |
| 13 | ~80% | 40.24 | 32.34 | 5.44 | 51% |
| 14 | ~20% | | inactive | 44.05 | 45% |
| 15 | >20% | inactive | 2.54 | 14.32 | 174 nM |

From these data, the activity profile of the compounds of this invention are seen to be that of antipsychotic agents with less potential for extra pyramidal side effects such as attend the use of major tranquillizers (sedation, pseudoparkinsonism, ataxia, muscle relaxation, etc.). This activity profile resembles that of the anxiolytic compound, buspirone. Further evidence that the pharmacological profile of the test compounds resembles that of buspirone was obtained by measuring the compound's ability to displace [³H] 8-OH DPAT (dipropylaminotetralin) from the 5-HT$_{1A}$ serotonin receptor by the procedure of Hall et al., *J. Neurochem.* 44: 1685–1696, 1985. Compounds of the invention, like buspirone, exhibited potent affinity for this serotonin receptor subtype. The anxiolytic activity of buspirone is currently believed to be due, at least in part, to this receptor (Vander Maclen et al., *Eur. J. Pharmacol.* 1986, 129(1-2)123–130. The test results of this study are as follows:

| Example | Inhibition of [³H] 8-OH DPAT Binding Ki, nM or % at 1 μM |
|---|---|
| 1 | 3 nM |
| 2 | 31 nM |
| 3 | 41 nM |
| 4 | 3.5 nM |
| 5 | 60 nM |
| 6 | 0.23 nM |
| 7 | 6.95 nM |
| 8 | 89% |
| 9 | 61% |
| 10 | 0.29 nM |
| 11 | 2.0 nM |
| 12 | 0.2 nM |
| 13 | 4 nM |
| 14 | 86% |
| 15 | 0.5 nM |

Hence, the compounds of this invention are antipsychotic agents and anxiolytic agents useful in the treatment of psychoses such as paranoia and schizophrenia and in alleviating anxiety. As such, they may be administered neat or with a pharmaceutical carrier to a patient in need thereof. The pharmaceutical carrier may be solid or liquid.

A solid carrier can include one or more substances which may also act as flavoring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavoring agents, suspending agents, thickening agents, colors, viscosity regulators, stabilisers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablets or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of representative compounds of this invention.

EXAMPLE 1

Hexahydro-3-[4-[4-(2-pyrimidinyl)-1-piperazinyl]-butyl]-1,5-methanocyclopent[d]azepine-2,4(1H,3H)-dione Bicyclo[3.3.0]-octane-2,4-dicarboxylic acid (1.6 g., 8.1 mmole) was converted to the anhydride by refluxing for three hours in 100 ml. of acetic anhydride. The excess reagent was removed in vacuo. Two hundred fifty (250) ml. of xylene was added along with 1.9 g. (8.1 mmole) of 1-(4-aminobutyl)-4-(2-pyrimidinyl)piperazine. The mixture was refluxed under nitrogen for 48 hours with water removal via a Dean-Stark trap. The solvent was then removed in vacuo and the residue filtered through 75 g. of silica gel with 2% ethanol/chloroform as eluent. Removal of solvent and recrystallization of the residue from isopropanol with the addition of 4N isopropanolic HCl, followed by a second recrystallization from isopropanol, gave 750 mg. of white solid title compound as hydrochloride, one quarter hydrate, m.p. 188°–189° C.

Analysis for: $C_{22}H_{31}N_5O_2 \cdot HCl \cdot \frac{1}{4}H_2O$: Calculated: C, 60.26; H, 7.47; N, 15.97. Found: C, 60.31; H, 7.32; N, 16.14.

EXAMPLE 2

Hexahydro-3-[4-[4-(6-chloro-2-pyrazinyl)-1-piperazinyl]butyl]-1,5-methanocyclopent[d]azepine-2,4(1H,3H)-dione The title compound was prepared from 4.58 g (25.4 mmoles) of bicyclo[3.3.0]-octane-2,4-dicarboxylic anhydride and 7.10 g (26 mmoles) of 1-(4-aminobutyl)-4-(6- chloro-2-pyrazinyl)-piperazine following the procedure in Example 1. 7.24 g of the hydrochloride salt was isolated as the one-quarter hydrate, m.p. 223°–225° C.

Analysis for: $C_{22}H_{30}N_5O_2Cl.HCl.\frac{1}{4}H_2O$: Calculated: C, 55.87; H, 6.71; N, 14.81. Found: C, 55.99; H, 6.58; N, 14.68.

EXAMPLE 3

Hexahydro-3-[4-[4-(2-pyrazinyl)-1-piperazinyl]butyl]-1,5-methanocyclopent[d]azepine-2,4(1H,3H)-dione The compound prepared in Example 2 (3 g., 7.0 mmol) was converted to the free base by washing a methylene chloride solution of the compound with saturated aqueous sodium bicarbonate and drying over $Na_2SO_4$. After filtration and evaporation in vacuo, the residue was redissolved in 200 ml. of ethanol and 4 ml. of triethylamine and 400 mg. of 10% palladium on carbon added. The mixture was hydrogenated at 60 p.s.i. for 5 hours, 200 mg. additional 10% Pd/C added, and hydrogenation continued for an additional 5 hours. The mixture was then filtered through celite and the solvent removed under vacuum. The residue was filtered through 75 g. of silica gel with 2% EtOH/CHCl$_3$ and the fractions containing product combined and concentrated. Recrystallization of the residue from isopropanol with the addition of 4N HCl in isopropanol gave 1.26 g. of white solid title compound as the hydrochloride salt, m.p. 212°–215° C.

Analysis for: $C_{22}H_{31}N_5O_2.HCl$: Calculated: C, 60.89; H, 7.43; N, 16.14. Found: C, 60.84; H, 7.49; N, 16.03.

EXAMPLE 4

5,5a,8,8a-Tetrahydro-3-[4-[4-(2-pyrimidinyl)-1-piperazinyl]butyl]1,5-methanocyclopent[d]azepine-2,4(1H,3H)-dione Bicyclo[3.3.0]oct-6-ene-2,4-dicarboxylic acid (12.6 g., 67 mmol.) was converted to 4.24 g. of anhydride by treatment with excess acetic anhydride as in Example 1. In this instance, however, the anhydride was purified by extraction of the dark residual gum with hexane, filtration, and evaporation in vacuo. The anhydride was combined with 6.0 g. (24 mmols) of 1-(4-aminobutyl)-4-(2-pyrimidinyl)piperazine in 250 ml. of xylene and refluxed under $N_2$ for 24 hours with water separation via a Dean-Stark trap. The supernatant liquid was removed at this point and replaced with an additional 150 ml. of xylene. Reflux under $N_2$ was continued for 24 hours. The combined xylene solutions were then evaporated and the residue column chromatographed on 250 g. of silica gel with a gradient elution beginning with CHCl$_3$ and ending with 10% CH$_3$OH/CHCl$_3$. The product-containing fractions were combined and evaporated and the residue crystallized from isopropanol with the addition of 4N HCl in isopropanol to give 3.25 g. of white solid title compound as the dihydrochloride salt, m.p. 232°–234° C.

Analysis for: $C_{22}H_{29}N_5O_2.2HCl$: Calculated: C, 56.41; H, 6.67; N, 14.95. Found: C, 56.51; H, 6.67; N, 15.27.

EXAMPLE 5

5,5a,8,8a-Tetrahydro-3-[4-[4-(6-chloro-2-pyrazinyl)-1-piperazinyl]butyl]-1,5-methanocyclopent[d]azepine-2,4(1H,3H)-dione The title compound was prepared from 2.1 g (12 mmoles) of bicyclo[3.3.0]oct-6-ene-2,4-dicarboxylic anhydride and 3.2 g (12 mmoles) of 1-(4-aminobutyl)-4-(6-chloro-2-pyrazinyl)piperazine following the procedure in Example 4. 620 mg of the hydrochloride salt was isolated as the hemihydrate, m.p. 222°–224° C., after two recrystallizations from isopropanol.

Analysis for: $C_{22}H_{28}N_5O_2.HCl.\frac{1}{2}H_2O$: Calculated: C, 55.58; H, 6.36; N, 14.73. Found: C, 55.78; H, 6.19; N, 14.72.

EXAMPLE 6

Decahydro-3-[4-[4-(2-pyrimidinyl)-1-piperazinyl]butyl]-1,5-methano-6,7,9-metheno-2H-pentaleno[1,2-d]azepine-2,4(3H)-dione Potassium permanganate (50 g., 0.32 mmoles) was dissolved in 500 ml. of water in a 1 l three neck flask equipped with a thermometer, addition funnel and overhead stirrer. To it was added a solution of 18.4 g. (0.10 mole) of norbornadiene dimer and 5.0 g. (0.018 mole) of tetra-n-butylammonium chloride in 300 ml. of benzene. The internal temperature was kept below 40° C. by means of a cold water bath. The reaction was stirred overnight at room temperature; then 60 g. of sodium bisulfite was added and the mixture acidified with concentrated hydrochloric acid. Five hundred milliliters of ethyl acetate was added and the organic phase was removed in a separatory funnel. The aqueous phase was extracted with two additional 500 ml. portions of ethyl acetate. The combined organic portions were washed with 300 ml. saturated brine, dried over $Na_2SO_4$, filtered, and evaporated to obtain 24 g. of 2,3,3a,4,5,6,6a,7,7a-decahydro-4,6,7-metheno-1H-cyclopenta[a]pentalene-1,3-dicarboxylic acid.

The diacid prepared above (2.5 g., 10 mmoles) was combined with 2.4 g. (10 mmoles) of 1-(4-aminobutyl)-4-(2-pyrimidinyl)piperazine in 300 ml. of xylene and refluxed under $N_2$ for 48 hours with water separation via a Dean-Stark trap. The mixture was allowed to cool, concentrated in vacuum and filtered through 75 g. of silica gel in 2% EtOH/CHCl$_3$. Concentration in vacuum and recrystallization from isopropanol with the addition of 4N HCl/isopropanol gave a pale pin solid title compound as the dihydrochloride, hemihydrate, 820 mg., m.p. 229°–231° C.

Analysis for: $C_{26}H_{33}N_5O_2.2HCl.\frac{1}{2}H_2O$: Calculated: C, 58.98; H, 6.85; N, 13.23. Found: C, 59.26; H, 6.78; N, 13.04.

EXAMPLE 7

Decahydro-3-[4-[4-(6-chloro-2-pyrazinyl)-1-piperazinyl]butyl]-1,5-methano-6,7,9-metheno-2H-pentaleno[1,2-d]azepine-2,4(3H)-dione 2.5 g. (10 mmole) of the diacid prepared in Example 6 was converted to the anhydride, octahydro-1,5-methano-6,8,9-methenopentaleno[1,2-d]oxepin-2,4(1H,5H)-dione, with acetic anhydride and coupled with 2.4 g (10 mmoles) of 1-(4-aminobutyl)-4-(6-chloro-2-pyrazinyl)piperazine following the procedure in Example 1. 1.7 g. of white solid title compound as the hydrochloride salt, m.p. 269°–270° C., was obtained.

Analysis for: $C_{26}H_{32}N_5O_2Cl.HCl$: Calculated: C, 60.23; H, 6.42; N, 13.51. Found: C, 59.94; H, 6.47; N, 13.57.

EXAMPLE 8

2,3,4,5-Tetrahydro-3-[4-[4-(2-pyrimidinyl)-1-piperazinyl]butyl]-1,5-methano-1H-3-benzazepine-2,4(3H, 5H)-dione 1,3-Indanedicarboxylic acid anhydride (1.9 g., 10 mmoles) was dissolved in methylene chloride and added to a solution of 1-(4-aminobutyl)-4-(2-pyrimidinyl)piperazine (3.0 g., 13 mmole) in the same solvent. The solvent was then removed in vacuo and replaced with 200 ml. of acetonitrile. Ethoxyacetylene (1 g., 14 mmole) was added and the mixture was refluxed under $N_2$ overnight. The solvent was then removed in vacuo and the residue redissolved in chloroform and filtered through 75 g. of silica gel. The column was washed with 1% MeOH/CHCl$_3$ and the extracts were combined and evaporated. The residue was crystallized from isopropanol with the addition of 4N HCl/isopropanol. A second recrystallization from isopropanol yielded 1.0 g. of tan solid title compound as the dihydrochloride salt, m.p. 259°–262° C.

Analysis for: $C_{23}H_{27}N_5O_2.2HCl$: Calculated: C, 57.74; H, 6.11; N, 14.64. Found: C, 57.65; H, 6.14; N, 14.71.

EXAMPLE 9

2,3,4,5-Tetrahydro-3-[4-[4-(6-chloro-2-pyrazinyl)-1-piperazinyl]butyl]-1,5-methano-1H-3-benzazepine-2,4(3H, 5H)-dione The title compound was prepared from 2.82 g. (15 mmoles) of 1,3-indanedicarboxylic acid anhydride and 4.04 g. (15 mmoles) of 1-(4-aminobutyl)-4-(6-chloro-2-pyrazinyl)piperazine following the procedure in Example 8. 1.37 g. of the title compound was obtained as the monohydrochloride, m.p. 225°–227° C.

Analysis for: $C_{23}H_{26}N_5O_2Cl.HCl$: Calculated: C, 57.99; H, 5.71; N, 14.70. Found: C, 57.87; H, 5.79; N, 14.59.

EXAMPLE 10

Decahydro-3-[4-[4-(2-methoxyphenyl)-1-piperazinyl]butyl]-1,5-methano-6,7,9-metheno-2H-pentaleno[1,2-d]azepine-2,4(3H)-dione 2.48 g. (10 mmoles) of 2,3,3a,3b,4,5,6,6a,7,7a-decahydro-4,6,7-metheno-1H-cyclopenta[a]pentalene-1,3-dicarboxylic acid was converted to the anhydride by refluxing with acetic anhydride and reacted with 1-(4-aminobutyl)-(2-methoxyphenyl)piperazine (2.63 g., 10 mmoles) according to the procedure in Example 1. 2.5 g. of the title compound was obtained as the dihydrochloride, hemihydrate, m.p. 220°–221° C.

Analysis for: $C_{29}H_{37}N_3O_3.2HCl.\frac{1}{2}H_2O$: Calculated: C, 62.47; H, 7.23; N, 7.54. Found: C, 62.20; H, 7.12; N, 7.50.

EXAMPLE 11

Hexahydro-3-[4-[4-(3-trifluoromethylphenyl)-1-piperazinyl]butyl]-1,5-methano-cyclopent[d]azepine-2,4(1H, 3H)-dione 2.5 g. (13 mmoles) of bicyclo[3.3.0]-octane-2,4-dicarboxylic acid was converted to the anhydride by refluxing with acetic anhydride and reacted with 3.4 g. (11.3 mmoles) of 1-(4-aminobutyl)-4-(3-trifluoromethylphenyl)piperazine according to the procedure in Example 1. 3.0 g. of the title compound was obtained as the monohydrochloride, quarter hydrate, m.p. 205°–207° C.

Analysis for: $C_{25}H_{32}N_3O_2F_3.HCl.\frac{1}{4}H_2O$: Calculated: C, 59.52; H, 6.69; N, 8.33. Found: C, 59.62; H, 6.75; N, 8.10.

EXAMPLE 12

Decahydro-3-[4-[4-(3-trifluoromethylphenyl)-1-piperazinyl]butyl]-1,5-methano-6,7,9-metheno-2H-pentaleno[1,2-d]azepine-2,4(3H)-dione 2.48 g. (10 mmoles) of 2,3,3a,3b,4,5,6,6a,7,7a-decahydro-4,6,7-metheno-1H-cyclopenta[a]pentalene-1,3-dicarboxylic acid was converted to the anhydride by refluxing with acetic anhydride and reacted with 3.0 g. (10 mmoles) of 1-(4-aminobutyl)-4-(3-trifluoromethylphenyl)piperazine according to the procedure in Example 1. 2.1 g. of the title compound was obtained as the monohydrochloride, m.p. 238°–239° C.

Analysis for: $C_{29}H_{34}N_3O_2F_3.HCl$: Calculated: C, 63.32; H, 6.41; N, 7.64. Found: C, 63.41; H, 6.58; N, 7.60.

EXAMPLE 13

Decahydro-3-[4-[4-(2-pyrazinyl)-1-piperazinyl]butyl]-1,5-methano-6,7,9-metheno-2H-pentaleno[1,2-d]azepine-2,4(3H)-dione 2.48 g. (10 mmoles) of 2,3,3a,3b,4,5,6,6a,7,7a-decahydro-4,6,7-metheno-1H-cyclopenta[a]pentalene-1,3-dicarboxylic acid was converted to the anhydride by refluxing with acetic anhydride and reacted with 2.35 g. (10 mmoles) of 1-(4-aminobutyl)-4-(2-pyrazinyl)piperazine according to the procedure in Example 1. Conversion to the salt by treatment with 4N isopropanolic HCl, followed by a second crystallization from isopropanol gave 670 mg. of the title compound as the monohydrochloride, hemihydrate, m.p. 231°–233° C.

Analysis for: $C_{26}H_{33}N_5O_2.HCl.\frac{1}{2}H_2O$: Calculated: C, 63.33; H, 7.16; N, 14.21. Found: C, 63.43; H, 7.09; N, 14.42.

EXAMPLE 14

Decahydro-3-[4-[4-(2-quinolyl)-1-piperazinyl]butyl]-1,5-methano-6,7,9-metheno-2H-pentaleno[1,2-d]azepine-2,4(3H)-dione 2.48 g. (10 mmoles) of 2,3,3a,3b,4,5,6,6a,7,7a-decahydro-4,6,7-metheno-1H-cyclopenta[a]pentalene-1,3-dicarboxylic acid was converted to the anhydride by refluxing with acetic anhydride and reacted with 2.84 g. (10 mmoles) of 1-(4-aminobutyl)-4-(2-quinolyl)piperazine according to the procedure in Example 1. Conversion to the salt by treatment with 4N isopropanolic HCl, followed by a second crystallization from isopropanol and a final recrystallization from ethanol gave 1.3 g. of the title compound as the dihydrochloride, ethanolate, m.p. 252°–255° C.

Analysis for: $C_{31}H_{36}N_4O_2.2HCl.C_2H_5OH$: Calculated: C, 64.38; H, 7.20; N, 9.10. Found: C, 64.36; H, 7.23; N, 8.97.

EXAMPLE 15

Octahydro-3-[4-[4-(2-pyrimidinyl)-1-piperazinyl]butyl]-2H-1,5:6,9-dimethano-2H-3-benzazepine-2,4(3H)-dione 5.26 g. (23.5 mmoles) of octahydro-endo-4,7-methanoindene-trans,trans-1,3-dicarboxylic acid was converted to the anhydride according to the procedure in Example 1, and this was purified by Kugelrohr distillation to give 4.67 g. (23 mmoles) of compound. The anhydride was reacted with 5.80 g. (25 mmoles) of 1-(4-aminobutyl)-4-(2-pyrimidinyl)piperazine as in Example 1 and the product purified by chromatography on 200 g. of silica gel using 2% methanol in chloroform as eluent. Three crops of crystalline free base totaling 2.4 g. were obtained by crystallization from isopropanol and these were combined and recrystallized from isopropanol with the addition of 4N isopropanolic HCl. 2.72 g. of dihydrochloride (m.p. 208°–210° C.) was obtained.

Analysis for: $C_{24}H_{33}N_5O_2.2HCl$: Calculated: C, 58.06; H, 7.11; N, 14.11. Found: C, 58.34; H, 7.40; N, 13.96.

What is claimed is:

1. A compound of the formula:

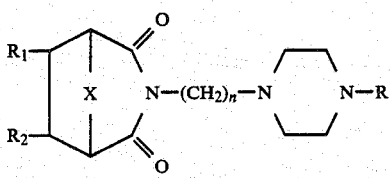

in which

X is $-O-$, $-S-$, $-SO-$, $-SO_2-$, $-CR_3R_4-$ where $R_3$ and $R_4$, independently, are hydrogen, alkyl of 1 to 4 carbon atoms or, taken together with the carbon atom to which they are attached, $R_3$ and $R_4$ form a cycloalkyl group of 3 to 5 carbon atoms;

n is one of the integers 2, 3, 4 or 5;

R is phenyl, halophenyl, trifluoromethylphenyl, alkoxyphenyl in which the alkoxy substituent contains 1 to 3 carbon atoms, 2-pyrimidinyl, halopyrimidin-2-yl, 2-pyrazinyl, halopyrazin-2-yl, 2-pyridinyl, halopyridin-2-yl, cyanopyridin-2-yl, quinolyl, or haloquinolyl;

$R_1$ and $R_2$, taken together, are alkylene of 3 to 5 carbon atoms or alkenylene of 3 to 5 carbon atoms, or taken with the carbon atoms to which they are attached, $R_1$ and $R_2$ complete a benzene ring, or a group of the formula:

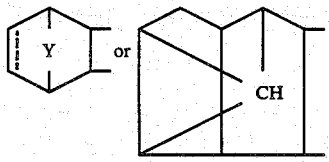

where Y is $-CH_2-$, $-CH_2-CH_2-$, $-O-$ or $-S-$ and the dotted line represents optional unsaturation; or a pharmaceutically acceptable salt thereof.

2. A compound of claim 1 of the formula:

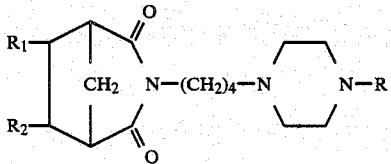

in which

R is 2-pyrimidinyl, halopyrimidin-2-yl, 2-pyrazinyl, chloropyrazin-2-yl, 2-pyridinyl, halopyridin-2-yl, or quinolyl;

$R_1$ and $R_2$, taken together, are alkylene of 3 to 5 carbon atoms or alkenylene of 3 to 5 carbon atoms, or taken with the carbon atoms to which they are attached, $R_1$ and $R_2$ complete a benzene ring; or a pharmaceutically acceptable salt thereof.

3. The compound of claim 1 which is hexahydro-3-[4-[4-(2-pyrimidinyl)-1-piperazinyl]butyl]-1,5-methanocyclopent[d]azepine-2,4(1H,3H)-dione.

4. The compound of claim 1 which is hexahydro-3-[4-[4-(6-chloro-2-pyrazinyl)-1-piperazinyl]butyl]-1,5-methanocyclopent[d]azepine-2,4(1H,3H)-dione.

5. The compound of claim 1 which is hexahydro-3-[4-[4-(2-pyrazinyl)-1-piperazinyl]butyl]-1,5-methanocyclopent[d]azepine-2,4(1H,3H)-dione.

6. The compound of claim 1 which is 5,5a,8,8a-tetrahydro-3-[4-[4-(2-pyrimidinyl)-1-piperazinyl]butyl]1,5-methanocyclopent[d]azepine-2,4(1H,3H)-dione.

7. The compound of claim 1 which is 5,5a,8,8a-tetrahydro-3-[4-[4-(6-chloro-2-pyrazinyl)-1-piperazinyl]butyl]-1,5-methanocyclopent[d]azepine-2,4(1H,3H)-dione.

8. The compound of claim 1 which is decahydro-3-[4-[4-(2-pyrimidinyl)-1-piperazinyl]butyl]-1,5-methano-6,7,9-metheno-2H-pentaleno[1,2-d]azepine-2,4(3H)-dione.

9. The compound of claim 1 which is decahydro-3-[4-[4-(6-chloro-2-pyrazinyl)-1-piperazinyl]butyl]-1,5-methano-6,7,9-metheno-2H-pentaleno[1,2-d]azepine-2,4(3H)-dione.

10. The compound of claim 1 which is 2,3,4,5-tetrahydro-3-[4-[4-(2-pyrimidinyl)-1-piperazinyl]butyl]-1,5-methano-1H-3-benzazepine-2,4(3H,5H)-dione.

11. The compound of claim 1 which is 2,3,4,5-tetrahydro-3-[4-[4-(6-chloro-2-pyrazinyl)-1-piperazinyl]butyl]-1,5-methano-1H-3-benzazepine-2,4(3H,5H)-dione.

12. The compound of claim 1 which is decahydro-3-[4-[4-(2-methoxyphenyl)-1-piperazinyl]butyl]-1,5-methano-6,7,9-metheno-2H-pentaleno[1,2-d]azepine-2,4(3H)-dione.

13. The compound of claim 1 which is hexahydro-3-[4-[4-(3-trifluoromethylphenyl)-1-piperazinyl]butyl-1,5-methano-cyclopent[d]azepine-2,4(1H,3H)-dione.

14. The compound of claim 1 which is decahydro-3-[4-[4-(3-trifluoromethylphenyl)-1-piperazinyl]butyl]-1,5-methano-6,7,9-metheno-2H-pentaleno[1,2-d]azepine-2,4(3H)-dione.

15. The compound of claim 1 which is decahydro-3-[4-[4-(2-pyrazinyl)-1-piperazinyl]butyl]-1,5-methano-6,7,9-metheno-2H-pentaleno[1,2-d]azepine-2,4(3H)-dione.

16. The compound of claim 1 which is decahydro-3-[4-[4-(2-quinolyl)-1-piperazinyl]butyl]-1,5-methano-6,7,9-metheno-2H-pentaleno[1,2-d]azepine-2,4(3H)-dione.

17. The compound of claim 1 which is octahydro-3-[4-[4-(2-pyrimidinyl)-1-piperazinyl]butyl]-2H-1,5:6,9-dimethano-2H-3-benzazepine-2,4(3H)-dione.

* * * * *